(12) United States Patent
Schulz et al.

(10) Patent No.: US 11,154,896 B2
(45) Date of Patent: Oct. 26, 2021

(54) AEROSOL GENERATOR

(71) Applicant: PARI Pharma GmbH, Starnberg (DE)

(72) Inventors: Harald Schulz, Tuttlingen (DE);
Philipp Holzmann, Munich (DE);
Dominique Mutschmann, Munich (DE); Michael Hahn, Krailling (DE)

(73) Assignee: PARI Pharma GmbH, Starnberg (DE)

( * ) Notice: Subject to any disclaimer, the term of this patent is extended or adjusted under 35 U.S.C. 154(b) by 754 days.

(21) Appl. No.: 15/955,973

(22) Filed: Apr. 18, 2018

(65) Prior Publication Data

US 2018/0236478 A1    Aug. 23, 2018

Related U.S. Application Data

(63) Continuation of application No. 14/123,634, filed as application No. PCT/EP2012/060488 on Jun. 4, 2012, now Pat. No. 9,975,136.

(30) Foreign Application Priority Data

Jun. 8, 2011 (EP) .................................... 1169080

(51) Int. Cl.
*B05B 17/00* (2006.01)
*A61M 11/00* (2006.01)
*A61M 15/00* (2006.01)

(52) U.S. Cl.
CPC ....... *B05B 17/0646* (2013.01); *A61M 11/005* (2013.01); *A61M 15/00* (2013.01);
(Continued)

(58) Field of Classification Search
CPC  A61M 11/005; A61M 15/00; A61M 15/0015; A61M 15/0018; A61M 15/0085;
(Continued)

(56) References Cited

U.S. PATENT DOCUMENTS 5,152,456 A    10/1992   Ross et al.
5,586,550 A    12/1996   Ivri et al.
(Continued)

FOREIGN PATENT DOCUMENTS

EP    1 293 257 A1    3/2003
EP    1 468 748 A1    10/2004
(Continued)

OTHER PUBLICATIONS

International Search Report and Written Opinion dated Sep. 5, 2012 in connection with International Application No. PCT/EP2012/060488.
(Continued)

*Primary Examiner* — Robert J Utama
*Assistant Examiner* — James F Sims, III
(74) *Attorney, Agent, or Firm* — Wolf, Greenfield & Sacks, P.C.

(57) ABSTRACT

An aerosol generator for generating an aerosol from a fluid, comprising: a vibratable membrane having a first side for being in contact with the fluid and an opposite second side, the membrane having a plurality of through holes penetrating the membrane in an extension direction from the first side to the second side, whereby the fluid passes the through holes from the first side to the second side when the membrane is vibrated for generating the aerosol at the second side, each through hole having along its extension direction a smallest diameter, a larger diameter that is larger than the smallest diameter and defined by that diameter that is closest to triple, preferably twice said smallest diameter, each through hole having a nozzle portion defined by that continuous portion of the through hole in the extension direction comprising the smallest diameter of the through hole and bordered by the larger diameter of the through hole, wherein the ratio of the total length of each through hole in
(Continued)

the extension direction to the length of a respective one of said nozzle portions in the extension direction is at least 4, preferably at least 4.5 and most preferred equal to or larger than 5.

23 Claims, 5 Drawing Sheets

(52) U.S. Cl.
CPC .... *A61M 15/0015* (2014.02); *A61M 15/0018* (2014.02); *A61M 15/0085* (2013.01)

(58) Field of Classification Search
CPC . B05B 17/0646; B05B 17/0638; B05B 17/06; B05B 17/0607
USPC .................................. 239/102.2; 128/200.16
See application file for complete search history.

(56) References Cited

U.S. PATENT DOCUMENTS

| | | | |
|---|---|---|---|
| 6,405,934 B1 | 6/2002 | Hess et al. | |
| 6,962,151 B1 | 11/2005 | Knoch et al. | |
| 9,975,136 B2 | 5/2018 | Schulz et al. | |
| 2001/0013554 A1 | 8/2001 | Borland et al. | |
| 2002/0157956 A1* | 10/2002 | Ikeda | C25D 1/08 205/75 |
| 2010/0044460 A1 | 2/2010 | Sauzade | |
| 2011/0111179 A1* | 5/2011 | Blick | B23K 26/55 428/172 |
| 2014/0263721 A1 | 9/2014 | Schulz et al. | |

FOREIGN PATENT DOCUMENTS

| | | |
|---|---|---|
| WO | WO 93/10910 A1 | 6/1993 |
| WO | WO 00/29167 A1 | 5/2000 |
| WO | WO 01/18280 A1 | 3/2001 |
| WO | WO 01/032246 A1 | 5/2001 |
| WO | WO 12/092163 A1 | 7/2012 |

OTHER PUBLICATIONS

International Preliminary Report on Patenatability dated Dec. 27, 2013 in connection with International Application No. PCT/EP2012/060488.

Humbach, "Mass production of metal microstructure products", Microproduction, 02/08, 2008, pp. 1-3.

Westermann, "New dimensions in electroforming", Microproduction, 02/11, 2011, pp. 26-29.

Third Party Observations dated Aug. 30, 2016 filed in European Application No. 12725433.2.

Third Party Observations dated Mar. 11, 2019 filed in European Application No. 12725433.2.

* cited by examiner

AEROSOL GENERATOR

CROSS REFERENCE TO RELATED APPLICATIONS

This application is a continuation of U.S. patent application Ser. No. 14/123,634 filed Apr. 22, 2014, which is a 371 of PCT/EP2012/060488 filed Jun. 4, 2012, which claims the priority benefit of European Application No. 11169080.6 filed Jun. 8, 2011, which are hereby incorporated by reference to the maximum extent allowable by law.

The present invention relates to an aerosol generator and in particular to an aerosol generator having a vibratable membrane with a plurality of through holes comprising a nozzle portion. More particularly the present invention relates to an optimized nozzle portion.

Aerosol generators are mainly used for industrial, laboratorial, and/or medical application, as well as in the field of consumer products but are not limited thereto. Especially the generation of efficient, reproducible and constant aerosol output for greater liquid volumes is currently insufficiently realized. In all applications which require a constant output or dose over the complete aerosol generation cycle (process) and reproducible output during every application an optimized aerosol generator is needed.

Aerosol generators having a vibratable membrane as described above and defined in the preamble of claim 1 are known by WO 93/10910 A1. The through holes defined in the vibratable membrane may be formed by electroforming such as disclosed in WO 01/18280 A1 or by means of a laser source as described for example in WO 00/29167 A1. Other techniques are, however, as well conceivable.

Further, it might turn out in dose finding studies that relatively high amounts of compound need to be delivered to a user. Yet, some liquids (e.g. medical substances or compounds) may not be administered at high concentration for different reasons. High concentration can be related to disadvantageous physico-chemical properties for the nebulization such as high viscosity (Newtonian fluid or non-Newtonian fluid like thixotrope). Further factors may be surface tension, density, kind of a fluid (solution or suspension), solubility or size of particles in the liquid (e.g. micro or nano suspension). A compound might not be solvable in high concentrations or more generally the liquid containing the compound might not be able to carry high concentrations of the compound (i.e. solution, suspension or colloidal drug formulation for an aerosol application and/or inhalation therapy, like liposomes, proteins, anti-bodies, emulsions, surfactants, viral shells and/or two vectors). Thus, in the administration a relatively large volume of fluid, particularly liquid, needs to be emitted in form of the aerosol. The liquid may contain substance or compounds, for example medical liquids, active substances, drugs or further compounds, such as for therapeutic, analytical and/or diagnostic applications. In standard aerosol generators, such as those mentioned in the above documents a relatively large period of time is required for emitting the entire liquid containing the compound in the form of an aerosol.

Such a long period of time, however, is perceived negative and uncomfortable by a user which can lead to a lower acceptance of the application (e.g. medical aerosol therapy, compromised patient compliance, potentially reduced efficacy of the medical aerosol therapy as well as print or fragrance aerosol applications).

Accordingly, the present invention aims to improve the known aerosol generators in this regard and to provide an aerosol generator that enables the emission of even constant large amounts of fluid, particularly liquid in the form of an aerosol in a shorter period of time.

This objective is resolved by an aerosol generator having the features as defined in claim 1. Embodiments of the present invention are defined in the dependent claims.

The present invention is based on the finding that the length of the nozzle portion of the through holes formed in the vibratable membrane has a significant influence on the total output rate (TOR) of the above aerosol generators. In particular, it has been found that the length of the nozzle portion is directly proportional to the total output rate, wherein the shorter the nozzle portion, the higher the TOR and vice versa. In contrast, it has been found that the diameter and the length of the portions upstream of the nozzle portion within the through hole do not have a significant influence on the TOR, if the nozzle portion is sufficiently short and small in diameter as compared to the upstream portion of the through hole. On the other hand, it has as well been found that the length of the nozzle portion as well has an influence on the geometric standard deviation (GSD) of the droplet size distribution. Low GSDs characterize a narrow droplet size distribution (homogeneously sized droplets), which is advantageous for targeting aerosol to the respiratory system. That is, the longer the nozzle portion the lower the GSD. The particle size (preferable below 5 µm) has a GSD in a range of 2.2 to 1.5.

In view of the above findings, the present invention suggests an aerosol generator for generating an aerosol particularly a medical aerosol, from a fluid, preferably a liquid. The aerosol generator comprises a vibratable membrane having a first side for being in contact with the fluid and an opposite second side, from which the droplets emerge. The membrane may be vibrated by means of a piezoelectric actuator or any other suitable means. The membrane has a plurality of through holes penetrating the membrane in an extension direction from the first side to the second side. The through holes may be formed as previously mentioned by a laser source, electroforming or any other suitable process. When the membrane is vibrating, the fluid passes the through holes from the first side to the second side to generate the aerosol at the second side. Each of the through holes has preferably an entrance opening and an exit opening, wherein a nozzle portion preferably extends from the exit opening over a portion of the through holes towards the entrance opening. The nozzle portion is defined by that continuous portion of the through hole in the extension direction comprising a smallest diameter of the through hole and bordered by a larger diameter of the through hole. The larger diameter of the through hole is defined as that diameter that is closest to triple, preferably only twice that smallest diameter. The smallest diameter of the through hole may correspond to the exit opening. Based on the above findings, the aerosol generator of the present invention has through holes in which the ratio of the total length of each through hole in the extension direction to the length of a respective one of said nozzle portions in the extension direction is at least 4, preferably at least 4.5 and most preferred equal to or larger than 5. In this context, at least 75%, more preferably 90%, even more preferably 95% of the through holes need to fulfill the above ratio. Yet, due to manufacturing intolerances some holes may fall outside the range. It has been proven that a ratio below 4, particularly when used in combination with high viscous fluids, high surface tension or fluids having physico-chemical properties which lead to a reduced TOR, may lead to insufficient and reduced nebulization and thus lengthens the nebulization time. Further, it has been found that a ratio of more than 10 will result in so-called bleeding. Bleeding in this context means that fluid passes the membrane from the first side to the second side even when the membrane is not vibrated. Thus, the second side of the membrane is wetted with fluid or liquid being counterproductive for the nebulization process. Preferred upper limits of the ratio are less than 8 and most preferred at about 6.5 or below. Further, it has been found that these ratios provide for an optimum of an increased TOR and a reasonably low GSD. Thus, this configuration enables to achieve shorter application periods and thus comfort for the patient and effectiveness of the medical compound. This is particularly advantageous if medical compounds are used which due to their physico-chemical properties lead to a reduced TOR or in which the concentration of the active compound is limited so that a greater volume of liquid containing the medical compound is to be administered.

According to one embodiment, it is preferred that the nozzle portion terminates flush with the second side. Hence, the length of the nozzle portion may be defined as that portion starting from the second side towards the first side up to and bordered by the diameter that it is closest to triple, preferably twice the smallest diameter. The smallest diameter will in these cases be located at the second side, as is the exit opening.

In any case, it is preferred that the smallest diameter, that is one border of the nozzle portion is located at that end of the nozzle portion in the extension direction adjacent to the second side and that the larger diameter of the through hole being the other border of the nozzle portion is located upstream of the smallest diameter in the direction in which the fluid passes the through holes during operation.

According to one embodiment, it is preferred that the smallest diameter is smaller than 4.5 µm.

In addition, it is preferred that the total length of a through hole in the extension direction is at least 50 µm, preferably at least 70 µm and most preferred at least 90 µm.

The length of the nozzle portion is preferably less than 25 µm, more preferred less than 20 µm and most preferred less than 15 µm.

According to one embodiment, the through holes may be laser-drilled through holes formed in at least two stages, one stage forming the nozzle portion and the remaining stage/-s forming the remainder of the through holes.

Yet, also other manufacturing methods may be used leading to a nozzle portion which is substantially cylindrical or conical with a tolerance of less than +100% of the smallest diameter, preferably less than +50% of the smallest diameter, more preferably less than +30% of the smallest diameter and most preferred less than +15% of the smallest diameter.

Alternatively, the through holes may as well be formed in an electroforming process. In this instant, but also using other manufacturing methods, the through holes may have a first funnel-shaped portion at the first side and a second funnel-shaped portion at the second side with the nozzle portion in-between the first and the second funnel-shaped portions and defined between the exit opening and the larger diameter. In this instance, the total length of the through holes may as well be defined by the distances from the first side to the exit opening (smallest diameter) only.

In addition, it has been found that the TOR may be further increased when increasing the number of through holes provided in the membrane. This may either be achieved by increasing the active perforated surface of the membrane and maintaining the distance of the through holes relative to each other at the same level, or by means of reducing the distance of the through holes relative to each other and maintaining the active area of the membrane. In addition, these measures may as well be combined. From this perspective, it is advantageous that the membrane comprises between 200 and 8,000 through holes, preferably between 1,000 and 6,000, and most preferred between 2,000 and 4,000 of the through holes. Preferably, more than 2,000 through holes are provided. This feature may as well be implemented in an aerosol generator having a nozzle portion different than described herein.

Further advantages and features, which may be implemented in an aerosol generator as described above in isolation or in combination with other features as long as the features do not contradict each other, are described in the following description of a preferred embodiment of the present invention. This description makes reference to the accompanying drawings, in which FIG. 1 shows a cross-sectional view of a generally known aerosol generator;

Figure 1:
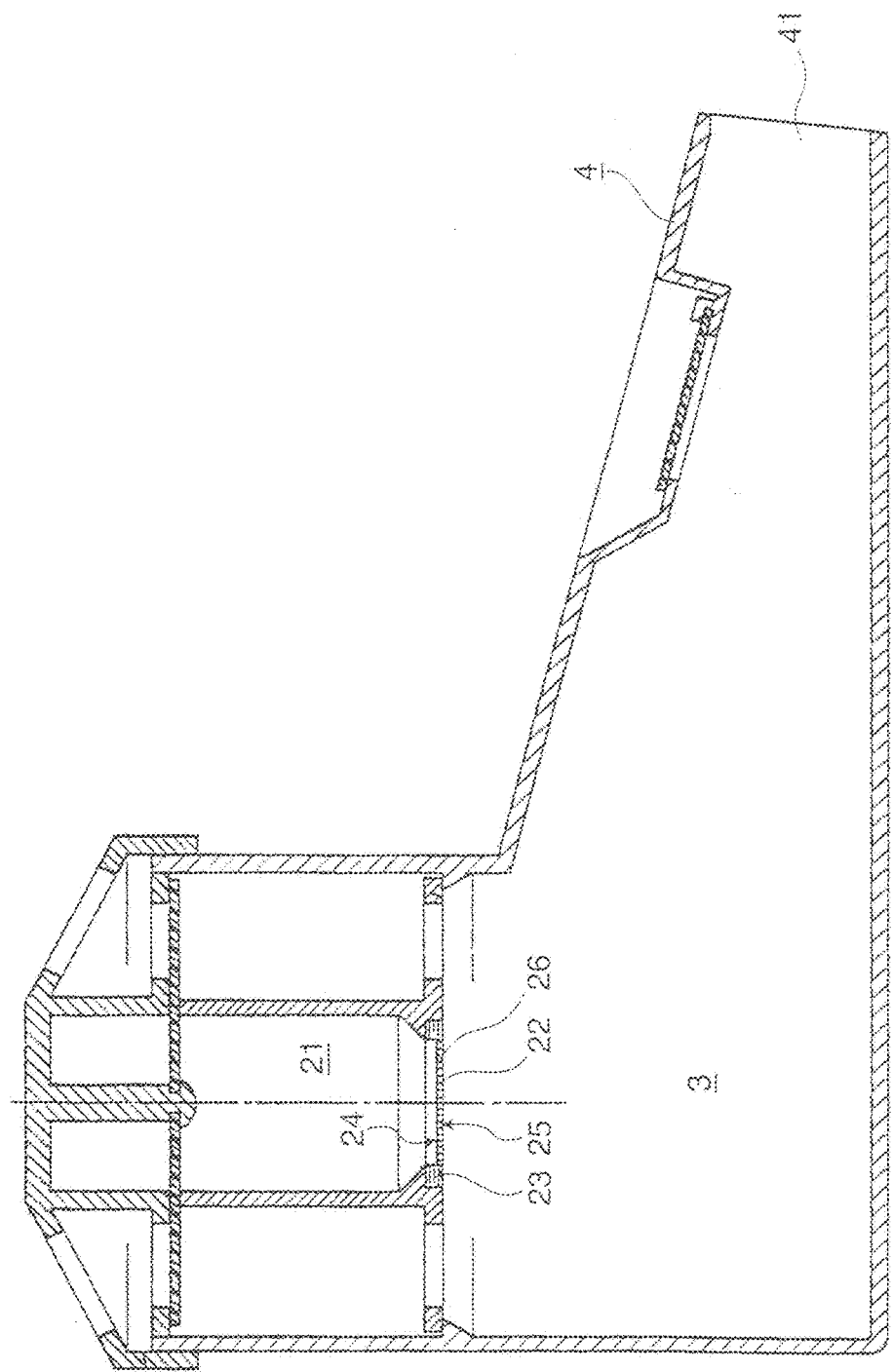

FIG. 1 shows an aerosol generator as disclosed in WO 2001/032246 A1, which is hereby incorporated by reference in its entirety. The aerosol generator comprises a fluid reservoir 21 to contain the fluid, particularly a liquid, to be emitted into the mixing chamber 3 in the form of an aerosol and to be inhaled by means of the mouth piece 4 through the opening 41.

The aerosol generator comprises a vibratable membrane 22 vibrated by means of a piezoelectric actuator 23. The vibratable membrane 22 has a first side 24 facing the fluid container 21 and a second opposite side 25 facing the mixing chamber 3. In use, the first side 24 of the vibratable membrane 22 is in contact with the fluid contained in the fluid container 21. A plurality of through holes 26 penetrating the membrane from the first side 24 to the second side 25 are provided in the membrane 22. In use, the fluid passes from the fluid container 21 through the through holes 26 from the first 24 to the second side 25 when the membrane 22 is vibrated for generating the aerosol at the second side 25 and emitting it into the mixing chamber 3. This aerosol may then be drawn by inhalation of a patient from the mixing chamber 3 via the mouth piece 4 and its inhalation opening 41.

Figure 2:
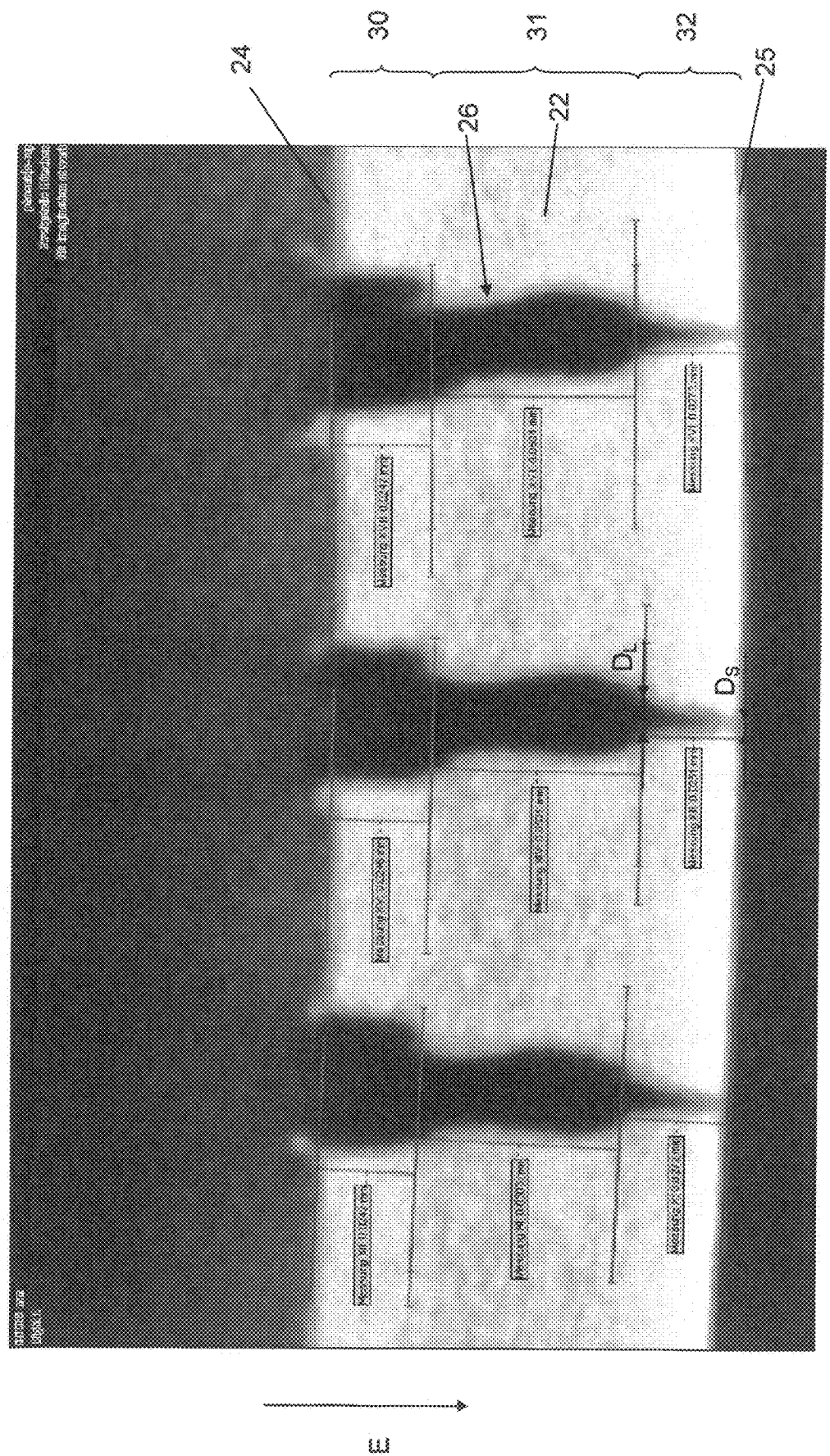
FIG. 2 is a computer tomography (CT) picture showing a membrane having a relatively long nozzle portion.

FIG. 2 shows a cross-sectional CT picture showing three of the through holes 26 of such a vibratable membrane 22. The through holes 26 of this particular embodiment are formed by laser drilling using three stages of different process parameters, respectively. In a first stage, the portion 30 is formed. In a second stage the portion 31 is formed and in a third stage the nozzle portion 32 is formed. In this particular embodiment, the average length of the nozzle portion 32 is 26 µm, whereas the portion 31 has an average length of 51 µm. The first portion 30 has an average length of 24.5 µm. As a result, the total length of each through hole is the sum of the length of the portion 30, the portion 31 and the nozzle portion 32, that is in this particular example 101.5 µm. Thus, the ratio of the total length of each through hole 26 in the extension direction E to the length of a respective one of the nozzle portions 32 in the extension direction E is approximately 3.9.

Figure 3:
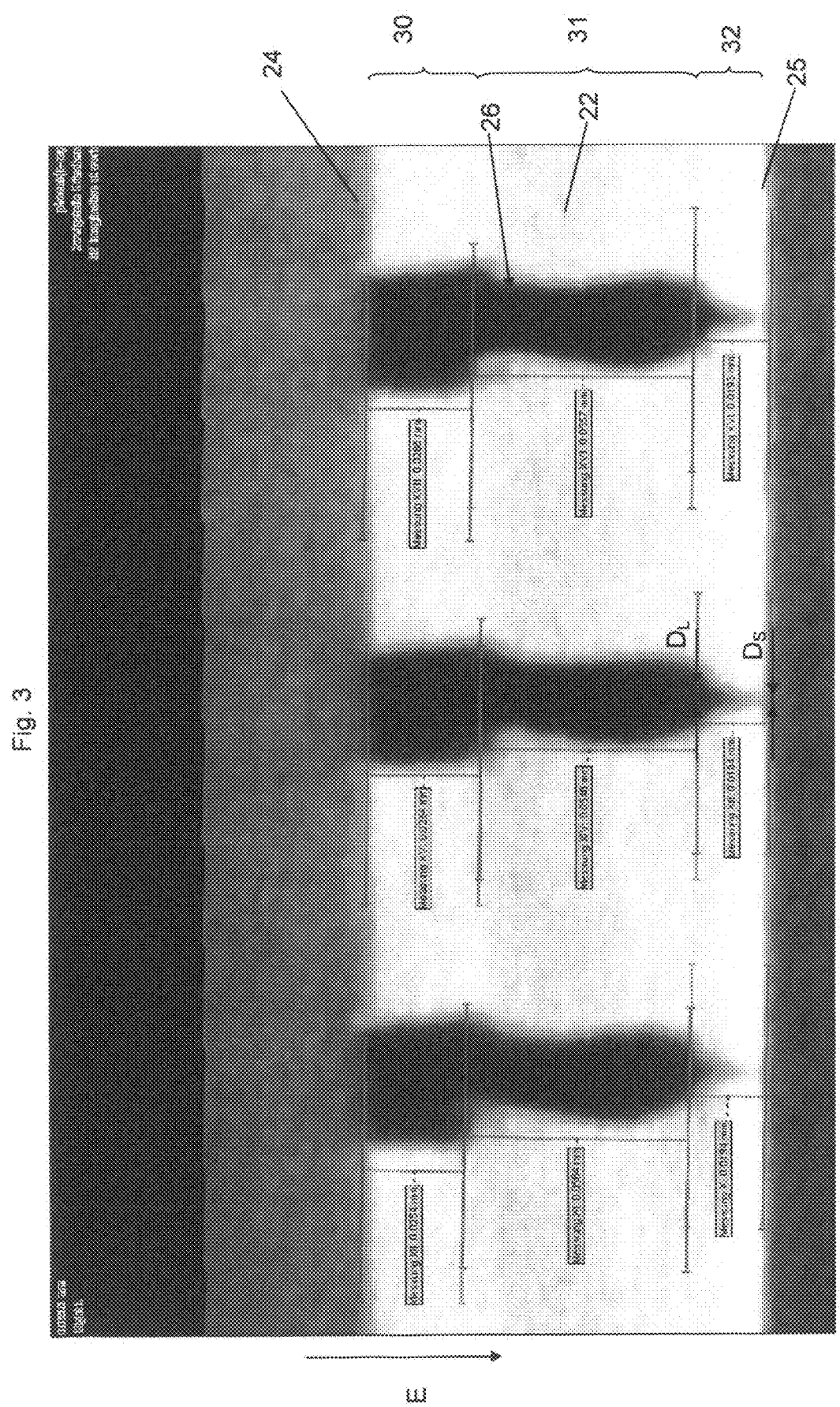
FIG. 3 is a computer tomography (CT) picture of another membrane having a relatively short nozzle portion.

In the embodiment in FIG. 3, however, the first portion 30 has a length of 27 µm, the portion 31 a length of 55 µm and a nozzle portion a length of 19 µm. As a result, the total length of the through hole 26 is 101 µm. Thus, the ratio of the total length of the through hole 26 to the length of the corresponding nozzle portion 32 in this embodiment is approximately 5.3.

Figure 4:
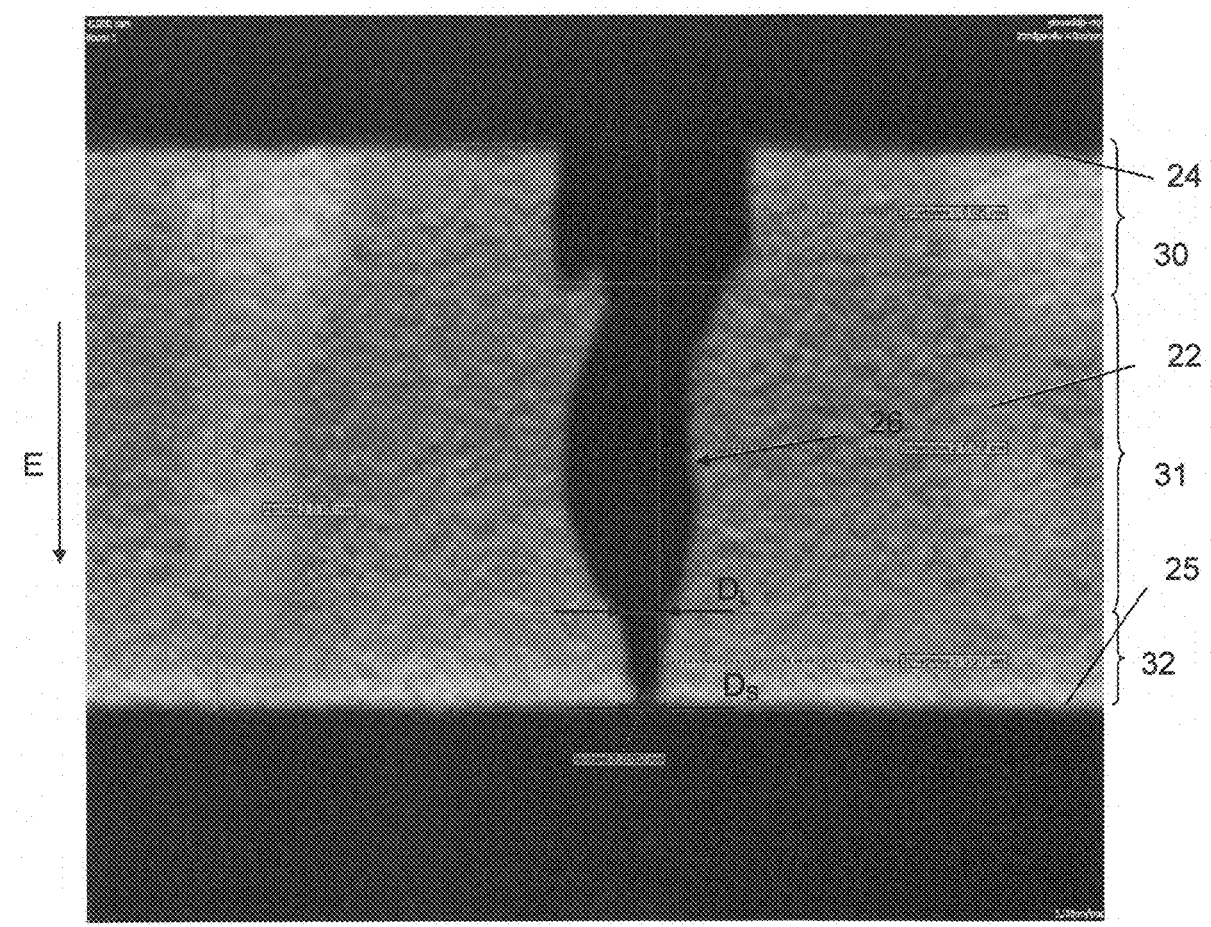
FIG. 4 is a computer tomography (CT) picture of another membrane having a relatively short nozzle portion.

In the embodiment in FIG. 4, however, the first portion 30 has a length of 25 µm, the portion 31 a length of 59 µm and a nozzle portion a length of 17 µm. As a result, the total length of the through hole 26 is 101 µm. Thus, the ratio of the total length of the through hole 26 to the length of the corresponding nozzle portion 32 in this embodiment is approximately 5.9.

Figure 5:
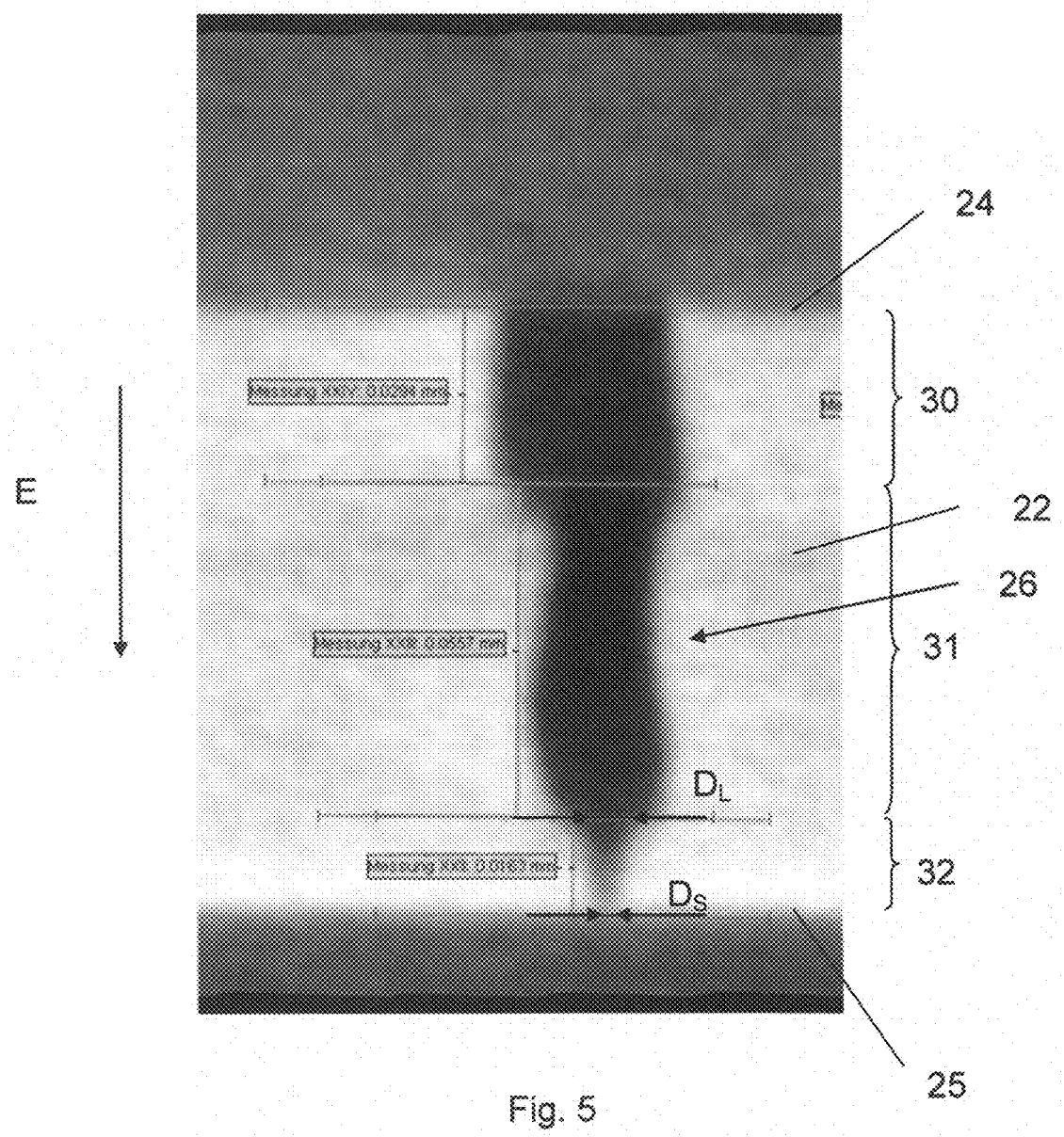
FIG. 5 is a computer tomography (CT) picture of another membrane having a relatively short nozzle portion.

In the embodiment in FIG. 5, however, the first portion 30 has a length of 29.4 µm, the portion 31 a length of 55.7 µm and a nozzle portion a length of 16.3 µm. As a result, the total length of the through hole 26 is 101.4 µm. Thus, the ratio of the total length of the through hole 26 to the length of the corresponding nozzle portion 32 in this embodiment is approximately 6.2.

Both the vibratable membranes in FIGS. 2,3 and 5 were manufactured with 6,000 through holes 26. The below table indicates the medium mass diameter (MMD) of the particles emitted at the second side of the membrane, the time required for completely emitting a certain amount of liquid (Neb Time) as well as the TOR. The tests were performed with ARIKACE™, which is a liposomal formulation of amikacine.

TABLE 1

| Membrane | MMD [µm] | Neb time [min] | TOR [g/min] | Number of through holes 26 |
| --- | --- | --- | --- | --- |
| 1 (shown in FIG. 2 with a nozzle portion of 26 µm) | 4.2 | 14.6 | 0.57 | 6,000 |
| 2 (shown in FIG. 3 with a nozzle portion of 19 µm) | 4.3 | 9.3 | 0.89 | 6,000 |
| 3 (similar to FIG. 3) | 4.4 | 13.4 | 0.62 | 3,000 |
| 4 (similar to FIG. 3) | 4.4 | 11.9 | 0.7 | 3,000 |
| 5 (shown in FIG. 4 with a nozzle portion of 17 µm) | 4.3 | 11.7 | 0.71 | 3,000 |
| 6 (shown in FIG. 5 with a nozzle portion of 16.3 µm) | 4.3 | 9.3 | 0.90 | 6,000 |

The above table shows that the membrane 2 and 6 with the shorter nozzle portion provides for an increased TOR and a reduced nebulization time by 5.3 minutes, that is approximately 36% less as compared to the membrane 1. The above table as well shows that the difference in the MMD is not significant as compared to the significant difference in the TOR. Thus, by means of the present invention, the nebulization time can be reduced significantly, without affecting the droplet size characteristics.

In addition to the membrane shown in FIGS. 2 and 3, membranes were manufactured having the nozzle portion further reduced but with 3,000 through holes 26 only. In particular, a membrane 3 had been laser-drilled with a shorter nozzle portion, whereas a membrane 4 had been manufactured using an even shorter nozzle portion. A further membrane 5 with 3,000 holes is shown in FIG. 4. From the above table, it becomes apparent that even with 3,000 holes (membrane 3,4 and 5) a reduction in the length of the nozzle portion results in an increased TOR compared to membrane 1 with 6,000 holes. The comparison of the membrane 3 and 4 as compared to the membrane 2 further shows that a combination of a higher number of holes (6,000 as compared to 3,000) and a reduced length of the nozzle portion has the strongest effect on increasing the TOR (membrane 2).

Further, it is advantageous to use a laser drilling process as compared to electroforming, as the through holes as shown in FIGS. 2 and 3 are substantially cylindrical or conical as compared to the funnel-shaped entrance and exit of electro-formed through holes as disclosed in WO 01/18280 A1. The vibration of the membrane, that is its vibration velocity, may be transferred to the liquid over a larger area by means of friction when the through holes are substantially cylindrical or conical as compared to the funnel-shaped entrance and exit of electro-formed through holes. The liquid is then because of its own inertia ejected from the exit openings of the through holes resulting in liquid jets collapsing to form the aerosol. Because of the extremely bent surface of the holes of an electro-formed membrane, the surface or area for transferring the energy from the membrane to the liquid is reduced. Yet, the present invention may as well be implemented in electro-formed membranes, wherein the nozzle portion is defined by that continuous portion of the through hole in the extension direction starting from the smallest diameter of the through hole towards the first side until it reaches a diameter triple or preferably only twice said smallest diameter. In this instance, the total length of the through hole is preferably measured from the smallest diameter to the first side.

The present invention of an aerosol generator can be used for different fluids, particularly liquids, for example for applications in the medical, pharmaceutical, diagnostic and/or analytical fields (e.g. human and veterinary aerosol therapies with drugs, substances or active compounds) as well as for agriculture, humidification, fragrance, hairspray, pyrotechnic, warfare agent, combustion engine, extinguishing, lubrication, adhesive, filtering, cooling, painting, printing, varnishing, coating processes, technologies and systems. Further examples are in the field of cell culture, pollen, herbal, medical, chemical, physical, biological, meteorological, pesticide, fungicide, biocide, toxic, environment, and exposition aerosol applications.

Among the active compounds which may be useful for serving one of the purposes named previously and that may be used together with the present invention, are, for example, substances selected from the group consisting of anti-inflammatory compounds, anti-infective agents, antiseptics, prostaglandins, endothelin receptor agonists, phosphodiesterase inhibitors, beta-2-sympathicomimetics, decongestants, vasoconstrictors, anticholinergics, immunomodulators, mucolytics, anti-allergic drugs, antihistaminics, mast-cell stabilizing agents, tumor growth inhibitory agents, wound healing agents, local anaesthetics, antioxidants, oligonucleotides, peptides, proteins, vaccines, vitamins, plant extracts, cholinesterase inhibitors, vasoactive intestinal peptide, serotonin receptor antagonists, and heparins, glucocorticoids, anti-allergic drugs, antioxidants, vitamins, leucotriene antagonists, anti-infective agents, antibiotics, antifungals, antivirals, mucolytics, decongestants, antiseptics, cytostatics, immunomodulators, vaccines, wound healing agents, local anaesthetics, oligonucleotides, xanthin derived agents, peptides, proteins and plant extracts. Such compound may be used in the form of a suspension, a solution, a colloidal formulation (i.e. liposomal), etc.

Examples of potentially useful anti-inflammatory compounds are glucocorticoids and non-steroidal anti-inflammatory agents such as betamethasone, beclomethasone, budesonide, ciclesonide, dexamethasone, desoxymethasone, fluocinolone acetonide, fluocinonide, flunisolide, fluticasone, icomethasone, rofleponide, triamcinolone acetonide, fluocortin butyl, hydrocortisone, hydroxycortisone-17-butyrate, prednicarbate, 6-methylprednisolone aceponate, mometasone furoate, dehydroepiandrosterone-sulfate (DHEAS), elastane, prostaglandin, leukotriene, bradykinin antagonists, non-steroidal anti-inflammatory drugs (NSAIDs), such as ibuprofen including any pharmaceutically acceptable salts, esters, isomers, stereoisomers, diastereomers, epimers, solvates or other hydrates, prodrugs, derivatives, or any other chemical or physical forms of active compounds comprising the respective active moieties.

Examples of anti-infective agents, whose class or therapeutic category is herein understood as comprising compounds which are effective against bacterial, fungal, and viral infections, i.e. encompassing the classes of antimicrobials, antibiotics, antifungals, antiseptics, and antivirals, are penicillins, including benzylpenicillins (penicillin-G-sodium, clemizone penicillin, benzathine penicillin G), phenoxypenicillins (penicillin V, propicillin), aminobenzylpenicillins (ampicillin, amoxycillin, bacampicillin), acylaminopenicillins (azlocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), and amidine penicillins (mecillinam);

cephalosporins, including cefazolins (cefazolin, cefazedone); cefuroximes (cefuroxim, cefamandole, cefotiam), cefoxitins (cefoxitin, cefotetan, latamoxef, flomoxef), cefotaximes (cefotaxime, ceftriaxone, ceftizoxime, cefmenoxime), ceftazidimes (ceftazidime, cefpirome, cefepime), cefalexins (cefalexin, cefaclor, cefadroxil, cefradine, loracarbef, cefprozil), and cefiximes (cefixime, cefpodoxim proxetile, cefuroxime axetil, cefetamet pivoxil, cefotiam hexetil), loracarbef, cefepim, clavulanic acid/amoxicillin, Ceftobiprole;

synergists, including beta-lactamase inhibitors, such as clavulanic acid, sulbactam, and tazobactam;

carbapenems, including imipenem, cilastin, meropenem, doripenem, tebipenem, ertapenem, ritipenam, and biapenem;

monobactams, including aztreonam;

aminoglycosides, such as apramycin, gentamicin, amikacin, isepamicin, arbekacin, tobramycin, netilmicin, spectinomycin, streptomycin, capreomycin, neomycin, paromoycin, and kanamycin;

macrolides, including erythromycin, clarythromycin, roxithromycin, azithromycin, dithromycin, josamycin, spiramycin and telithromycin;

gyrase inhibitors or fluroquinolones, including ciprofloxacin, gatifloxacin, norfloxacin, ofloxacin, levofloxacin, perfloxacin, lomefloxacin, fleroxacin, garenoxacin, clinafloxacin, sitafloxacin, prulifloxacin, olamufloxacin, caderofloxacin, gemifloxacin, balofloxacin, trovafloxacin, and moxifloxacin;

tetracyclins, including tetracyclin, oxytetracyclin, rolitetracyclin, minocyclin, doxycycline, tigecycline and aminocycline;

glycopeptides, including vancomycin, teicoplanin, ristocetin, avoparcin, oritavancin, ramoplanin, and peptide 4;

polypeptides, including plectasin, dalbavancin, daptomycin, oritavancin, ramoplanin, dalbavancin, telavancin, bacitracin, tyrothricin, neomycin, kanamycin, mupirocin, paromomycin, polymyxin B and colistin;

sulfonamides, including sulfadiazine, sulfamethoxazole, sulfalene, co-trimoxazole, co-trimetrol, co-trimoxazine, and co-tetraxazine;

azoles, including clotrimazole, oxiconazole, miconazole, ketoconazole, itraconazole, fluconazole, metronidazole, tinidazole, bifonazol, ravuconazol, posaconazol, voriconazole, and ornidazole and other antifungals including flucytosin, griseofulvin, tolnaftat, naftifin, terbinafin, amorolfin, ciclopiroxolamin, echinocandins, such as micafungin, caspofungin, anidulafungin;

nitrofurans, including nitrofurantoin and nitrofuranzone;

polyenes, including amphotericin B, natamycin, nystatin, flucocytosine; flucytosine other antibiotics, including tithromycin, lincomycin, clindamycin, oxazolidinones (linzezolids), ranbezolid, streptogramine A+B, pristinamycin A+B, Virginiamycin A+B, dalfopristin/quinupristin (Synercid), chloramphenicol, ethambutol, pyrazinamid, terizidon, dapson, prothionamid, fosfomycin, fucidinic acid, rifampicin, isoniazid, cycloserine, terizidone, ansamycin, lysostaphin, iclaprim, mirocin B17, clerocidin, filgrastim, and pentamidine;

antivirals, including aciclovir, ganciclovir, birivudin, valaciclovir, zidovudine, didanosin, thiacytidin, stavudin, lamivudin, zalcitabin, ribavirin, nevirapirin, delaviridin, trifluridin, ritonavir, saquinavir, indinavir, foscarnet, amantadin, podophyllotoxin, vidarabine, tromantadine, and proteinase inhibitors, siRNA-based drugs;

antiseptics, including acridine derivatives, iodine-povidone, benzoates, rivanol, chlorhexidine, quarternary ammonium compounds, cetrimides, biphenylol, clorofene, and octenidine;

plant extracts or ingredients, such as plant extracts from chamomile, hamamelis, echinacea, calendula, thymian, papain, pelargonium, pine trees, essential oils, myrtol, pinen, limonen, cineole, thymol, mentol, camphor, tannin, alpha-hederin, bisabolol, lycopodin, vitapherole;

wound healing compounds including dexpantenol, allantoin, vitamins, hyaluronic acid, alpha-antitrypsin, anorganic and organic zinc salts/compounds, salts of bismuth and selen interferones (alpha, beta, gamma), tumor necrosis factors, cytokines, interleukines;

immunmodulators including methotrexat, azathioprine, cyclosporine, tacrolimus, sirolimus, rapamycin, mofetil; mofetil-mycophenolate.

cytostatics and metastasis inhibitors;

alkylants, such as nimustine, melphalane, carmustine, lomustine, cyclophosphamide, ifosfamide, trofosfamide, chlorambucil, busulfane, treosulfane, prednimustine, thiotepa;

antimetabolites, e.g. cytarabine, fluorouracil, methotrexate, mercaptopurine, tioguanine;

alkaloids, such as vinblastine, vincristine, vindesine;

antibiotics, such as alcarubicine, bleomycine, dactinomycine, daunorubicine, doxorubicine, epirubicine, idarubicine, mitomycine, plicamycine;

complexes of transition group elements (e.g. Ti, Zr, V, Nb, Ta, Mo, W, Pt) such as carboplatinum, cis-platinum and metallocene compounds such as titanocendichloride;

amsacrine, dacarbazine, estramustine, etoposide, beraprost, hydroxycarbamide, mitoxanthrone, procarbazine, temiposide;

paclitaxel, gefitinib, vandetanib, erlotinib, poly-ADP-ribose-polymerase (PRAP) enzyme inhibitors, banoxantrone, gemcitabine, pemetrexed, bevacizumab, ranibizumab.

Examples of potentially useful mucolytics are DNase, P2Y2-agonists (denufosol), drugs affecting chloride and sodium permeation, such as N-(3,5-Diamino-6-chloropyrazine-2-carbony)-N'-{4-[4-(2,3-dihydroxypropoxy)-phenyl]butyl}guanidine methanesulfonate (PARION 552-02), heparinoids, guaifenesin, acetylcysteine, carbocysteine, ambroxol, bromhexine, tyloxapol, lecithins, myrtol, and recombinant surfactant proteins.

Examples of potentially useful vasoconstrictors and decongestants which may be useful to reduce the swelling of the mucosa are phenylephrine, naphazoline, tramazoline, tetryzoline, oxymetazoline, fenoxazoline, xylometazoline, epinephrine, isoprenaline, hexoprenaline, and ephedrine.

Examples of potentially useful local anaesthetic agents include benzocaine, tetracaine, procaine, lidocaine and bupivacaine.

Examples of potentially useful antiallergic agents include the afore-mentioned glucocorticoids, cromolyn sodium, nedocromil, cetrizin, loratidin, montelukast, roflumilast, ziluton, omalizumab, heparinoids and other antihistamins, including azelastine, cetirizin, desloratadin, ebastin, fexofenadin, levocetirizin, loratadin.

Examples of potentially useful anticholinergic agents include ipratropium bromide, tiotropium bromide, oxitropium bromide, glycopyrrolate Examples of potentially useful beta-2-sympathicomimetic agents include salbutamol, fenoterol, formoterol, isoproterenol, metaproterenol, salmeterol, terbutaline, clenbuterol, isoetarine, pirbuterol, procaterol, ritodrine, Examples of xanthin derived agents include theophylline, theobromine, caffeine This list, however, is not exhaustive.

The invention claimed is:

1. A method of manufacturing a vibratable membrane for use in an aerosol generator for generating an aerosol from a fluid, comprising:
providing a vibratable membrane having a first side for contact with the fluid and an opposite second side, and
providing the membrane with a plurality of through holes penetrating the membrane from the first side to the second side, whereby the fluid passes the through holes from the first side to the second side when the membrane is vibrated for generating the aerosol at the second side, each through hole having a nozzle portion, wherein
a ratio of a total length of each through hole to a length of the nozzle portion is at least 4, and wherein
the through holes are formed using a laser drilling process including at least two laser drilling stages for forming each of the through holes.

2. The method of claim 1, wherein the nozzle portion is formed to be substantially cylindrical or conical.

3. The method of claim 1, wherein the through holes are formed to have two or more portions and the nozzle portion.

4. The method of claim 1, wherein one end of the nozzle portion is formed to terminate flush with the second side.

5. The method of claim 1, wherein the total length of the through holes is at least 50 µm.

6. The method of claim 1, wherein the total length of the through holes is at least 70 µm.

7. The method of claim 1, wherein the total length of the through holes is at least 90 µm.

8. The method of claim 1, wherein the at least two laser drilling stages have different process parameters.

9. The method of claim 8, wherein the ratio of the total length of each through hole to the length of the nozzle portion is in a range of 4 to 10.

10. The method of claim 1, wherein the length of the nozzle portion is less than 25 µm.

11. The method of claim 1, wherein the length of the nozzle portion is less than 20 µm.

12. The method of claim 1, wherein the length of the nozzle portion is less than 15 µm.

13. A method of manufacturing a vibratable membrane for use in an aerosol generator for generating an aerosol from a fluid, comprising:
providing a vibratable membrane having a first side for contact with the fluid and an opposite second side, and
providing the membrane with a plurality of through holes penetrating the membrane from the first side to the second side, whereby the fluid passes the through holes from the first side to the second side when the membrane is vibrated for generating the aerosol at the second side, each through hole having a first portion, a second portion and a nozzle portion, wherein
a ratio of a total length of each through hole to a length of the nozzle portion is at least 4, and wherein
the through holes are formed using a laser drilling process including a first laser drilling stage for forming the first portion of each through hole, a second laser drilling stage for forming the second portion of each through hole and a third laser drilling stage for forming the nozzle portion of each through hole.

14. The method of claim 13, wherein the nozzle portion is formed to be substantially cylindrical or conical.

15. The method of claim 13, wherein one end of the nozzle portion is formed to terminate flush with the second side.

16. The method of claim 13, wherein the total length of the through holes is at least 50 µm.

17. The method of claim 13, wherein the total length of the through holes is at least 70 µm.

18. The method of claim 13, wherein the total length of the through holes is at least 90 µm.

19. The method of claim 13, wherein the first, second and third laser drilling stages have different process parameters.

20. The method of claim 19, wherein the ratio of the total length of each through hole to the length of the nozzle portion is in a range of 4 to 10.

21. The method of claim 13, wherein the length of the nozzle portion is less than 25 µm.

22. The method of claim 13, wherein the length of the nozzle portion is less than 20 µm.

23. The method of claim 13, wherein the length of the nozzle portion is less than 15 µm.

* * * * *

UNITED STATES PATENT AND TRADEMARK OFFICE
CERTIFICATE OF CORRECTION

| | | |
|---|---|---|
| PATENT NO. | : 11,154,896 B2 | Page 1 of 1 |
| APPLICATION NO. | : 15/955973 | |
| DATED | : October 26, 2021 | |
| INVENTOR(S) | : Harald Schulz et al. | |

It is certified that error appears in the above-identified patent and that said Letters Patent is hereby corrected as shown below:

On the Title Page

In item (30), Foreign Application Priority Data, please replace:
"Jun. 8, 2011 (EP) .............................. 1169080"

With:
--Jun. 8, 2011 (EP) .............................. 11169080--.

Signed and Sealed this
Fifth Day of September, 2023

Katherine Kelly Vidal
*Director of the United States Patent and Trademark Office*